(12) United States Patent
Wendlandt et al.

(10) Patent No.: US 10,377,866 B2
(45) Date of Patent: Aug. 13, 2019

(54) FLUOROPOLYMER ARTICLES HAVING A HIGH SURFACE ROUGHNESS AND HIGH COARSENESS

(71) Applicants: W. L. Gore & Associates GmbH, Putzbrunn (DE); W. L. Gore & Associates, Inc., Newark, DE (US)

(72) Inventors: Michael Wendlandt, Ottobrunn (DE); Wolfgang Bürger, Burgrain (DE); John William Dolan, Greenville, DE (US)

(73) Assignees: W. L. Gore & Associates, Inc., Newark, DE (US); W. L. Gore & Associates GmbH, Putzbrunn (DE)

( * ) Notice: Subject to any disclaimer, the term of this patent is extended or adjusted under 35 U.S.C. 154(b) by 621 days.

(21) Appl. No.: 14/051,529

(22) Filed: Oct. 11, 2013

(65) Prior Publication Data

US 2014/0120286 A1  May 1, 2014

(30) Foreign Application Priority Data

Oct. 31, 2012  (EP) .................................... 12007447

(51) Int. Cl.
  *C08J 5/00* (2006.01)
  *C08K 5/01* (2006.01)
  (Continued)

(52) U.S. Cl.
  CPC .............. *C08J 5/00* (2013.01); *A61C 15/041* (2013.01); *B01D 67/0009* (2013.01);
  (Continued)

(58) Field of Classification Search
  CPC .............. A61C 15/041; B01D 2325/06; B01D 67/0009; B01D 67/0027; B01D 69/02;
  (Continued)

(56) References Cited

U.S. PATENT DOCUMENTS 3,953,566 A  4/1976 Gore
4,482,516 A * 11/1984 Bowman .............. B29C 55/005
                                                   264/127

(Continued)

FOREIGN PATENT DOCUMENTS

| JP | 1989-178534 | 12/1987 |
| JP | 1997-501861 | 2/1997 |
| JP | 2006281202 | 10/2006 |

OTHER PUBLICATIONS

International Search Report for International Application No. PCT/EP2013/003217 dated Dec. 20, 2013.

(Continued)

*Primary Examiner* — Yan Lan
(74) *Attorney, Agent, or Firm* — Amy L. Miller

(57) ABSTRACT

Fluoropolymer articles having a high surface roughness and high coarseness are provided. In one embodiment, a fiber is provided that has a surface roughness expressed as a peak-to-valley distance (Rt) greater than 10 micrometers and an average surface roughness (Ra) greater than 1.5 micrometers. In another embodiment, a membrane having a coarseness index ρ/EBP of at least 0.3 g/cm³/psi and an air permeability of 15 ft³/ft²/min or higher is provided. The fluoropolymer articles are produced by a process that includes forming a paste-formed fluoropolymer product at a temperature lower than 50° C., densifying the paste-formed product, and then stretching the densPied paste-formed fluoropolymer product in at least one direction. In exemplary embodiments, the fluoropolymer may be polytetrafluoroethylene (PTFE), a modified PTFE, a TFE copolymer, a fluorothermoplastic, a fluoroelastomer, or combinations thereof.

8 Claims, 8 Drawing Sheets

(Fiber F3)

(51) Int. Cl.
*D01F 6/12* (2006.01)
*D01D 5/16* (2006.01)
*B01D 67/00* (2006.01)
*B01D 69/02* (2006.01)
*B01D 71/32* (2006.01)
*D01D 5/42* (2006.01)
*A61C 15/04* (2006.01)

(52) U.S. Cl.
CPC ......... *B01D 67/0027* (2013.01); *B01D 69/02* (2013.01); *B01D 71/32* (2013.01); *C08K 5/01* (2013.01); *D01D 5/16* (2013.01); *D01D 5/426* (2013.01); *D01F 6/12* (2013.01); *B01D 2325/06* (2013.01); *Y10T 428/139* (2015.01); *Y10T 428/24355* (2015.01); *Y10T 428/2978* (2015.01)

(58) Field of Classification Search
CPC .. B01D 71/32; C08J 5/00; C08K 5/01; D01D 5/16; D01D 5/426; Y10T 428/139; Y10T 428/24355; Y10T 428/2978
See application file for complete search history.

(56) References Cited

U.S. PATENT DOCUMENTS

| | | | |
|---|---|---|---|
| 4,598,011 A | 7/1986 | Bowman | |
| 5,518,012 A * | 5/1996 | Dolan | A61C 15/041 132/321 |
| 5,708,044 A * | 1/1998 | Branca | B29C 55/005 264/127 |
| 5,814,405 A | 9/1998 | Branca et al. | |
| 6,573,311 B1 * | 6/2003 | Martakos | A61F 2/06 264/423 |
| 7,060,354 B2 * | 6/2006 | Baillie | A61C 15/041 132/321 |
| 7,445,843 B2 * | 11/2008 | Lutz | A01K 91/00 428/364 |
| 2006/0032813 A1 * | 2/2006 | Ieraci | B01D 67/0086 210/500.36 |
| 2009/0241983 A1 | 10/2009 | Williiams et al. | |

OTHER PUBLICATIONS

EP Search Report for Application No. EP 12 00 7447 dated Mar. 19, 2013.
S. J. Ledermann, M. M. Taylor (1972), Perception & Psychophysics, vol. 12 (5), p. 401-408.
S. Ebnesajjad (2000) Fluroplastics, vol. 1; Non-Melt Processible Fluoroplastics, Chapter 8.3 pp. 150-152; Plastics Design Library.
Ariwan, Alfonsius B; Ebnesajjad, Sina; and Hatzikiriakos, Savvas; Rheology of Polytetrafluoroethylene as related to Paste Extrusion.
Ariwan, Alfonsius B; Ebnesajjad, Sina; and Hatzikiriakos, Savvas; Properties of Polytetrafluoroethylene (PTFE) Paste Extrudates, Polymer Engineering and Science, Jun. 2002, vol. 42 No. 6.
Lederman, Susan J., Tactual Roughness Perception: Apatial and Temporal Determinants, Canadian Journal of Pschology, 1983, 37 (4), pp. 498-511.
Smith-Wormald, "Geometric separator theorems and applications" Apr. 29, 1998, pp. 1-51.

* cited by examiner

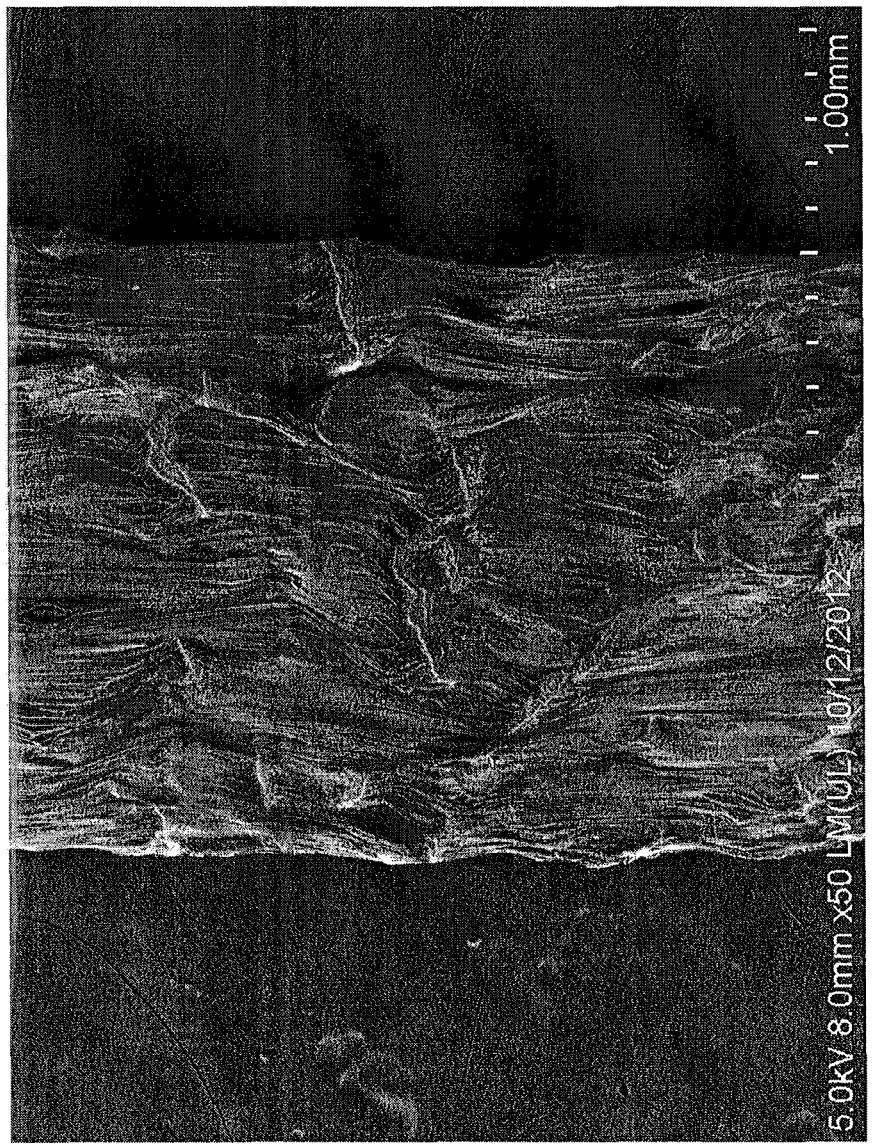
Fig. 1 (Fiber F3)

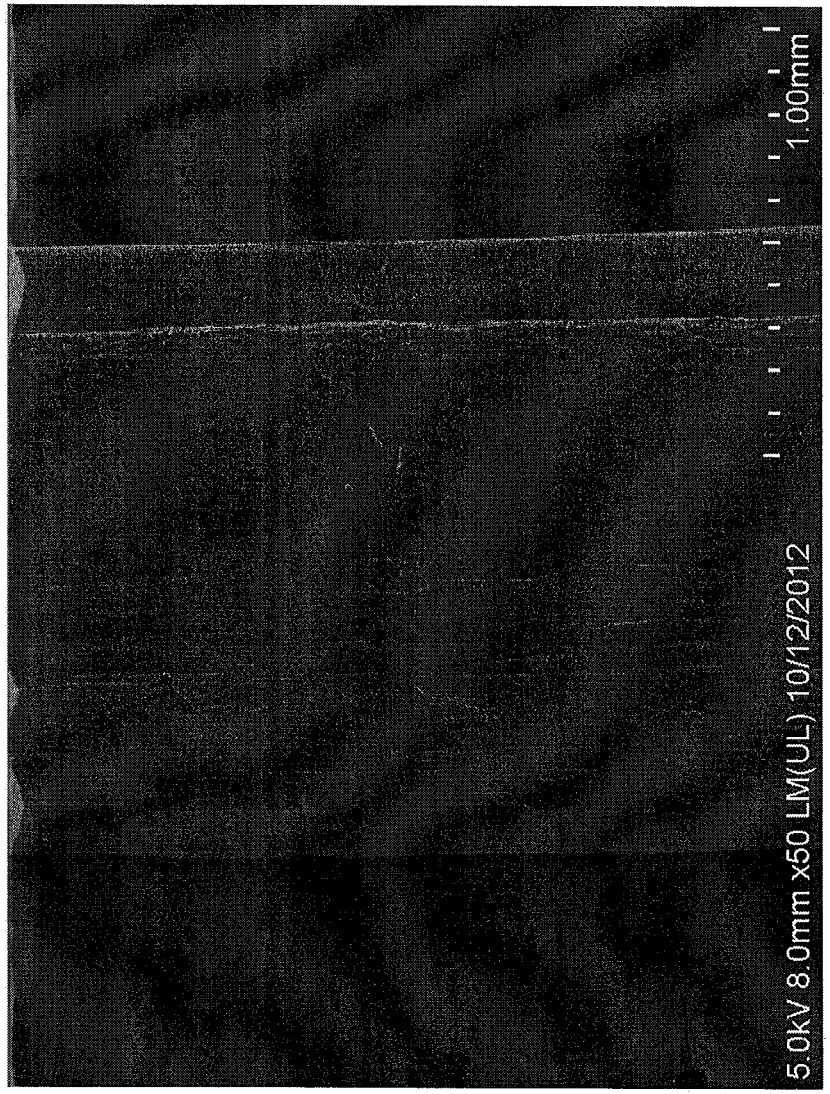
Fig. 2 (Fiber F1)

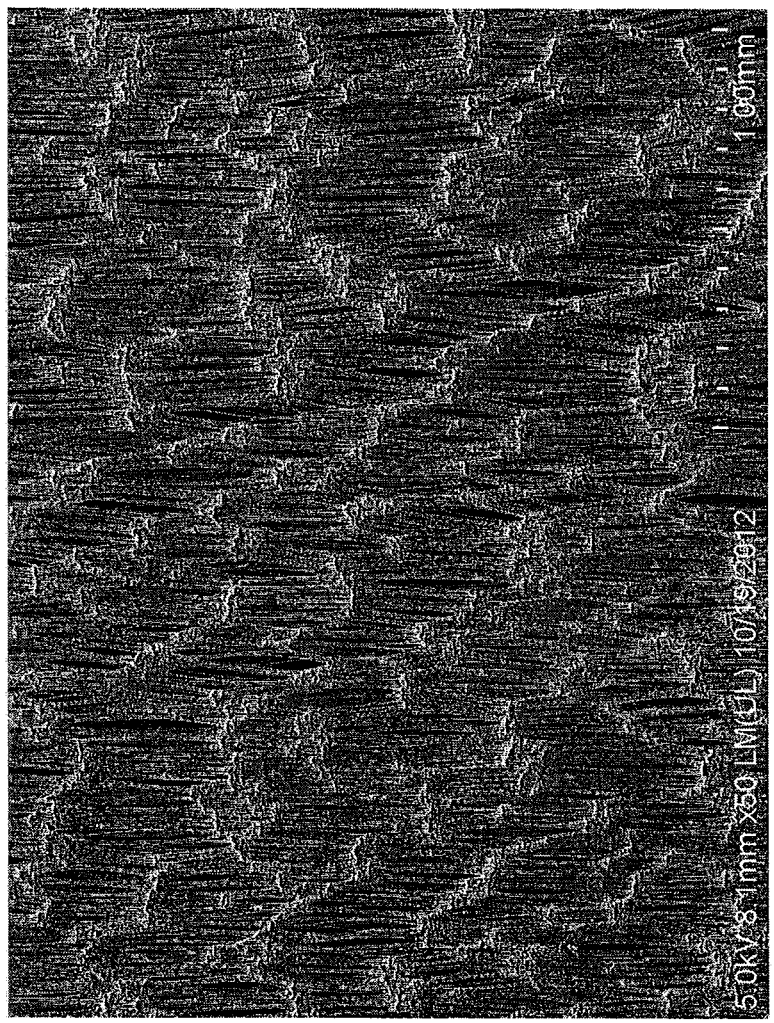
Fig. 3 (Tape T5)

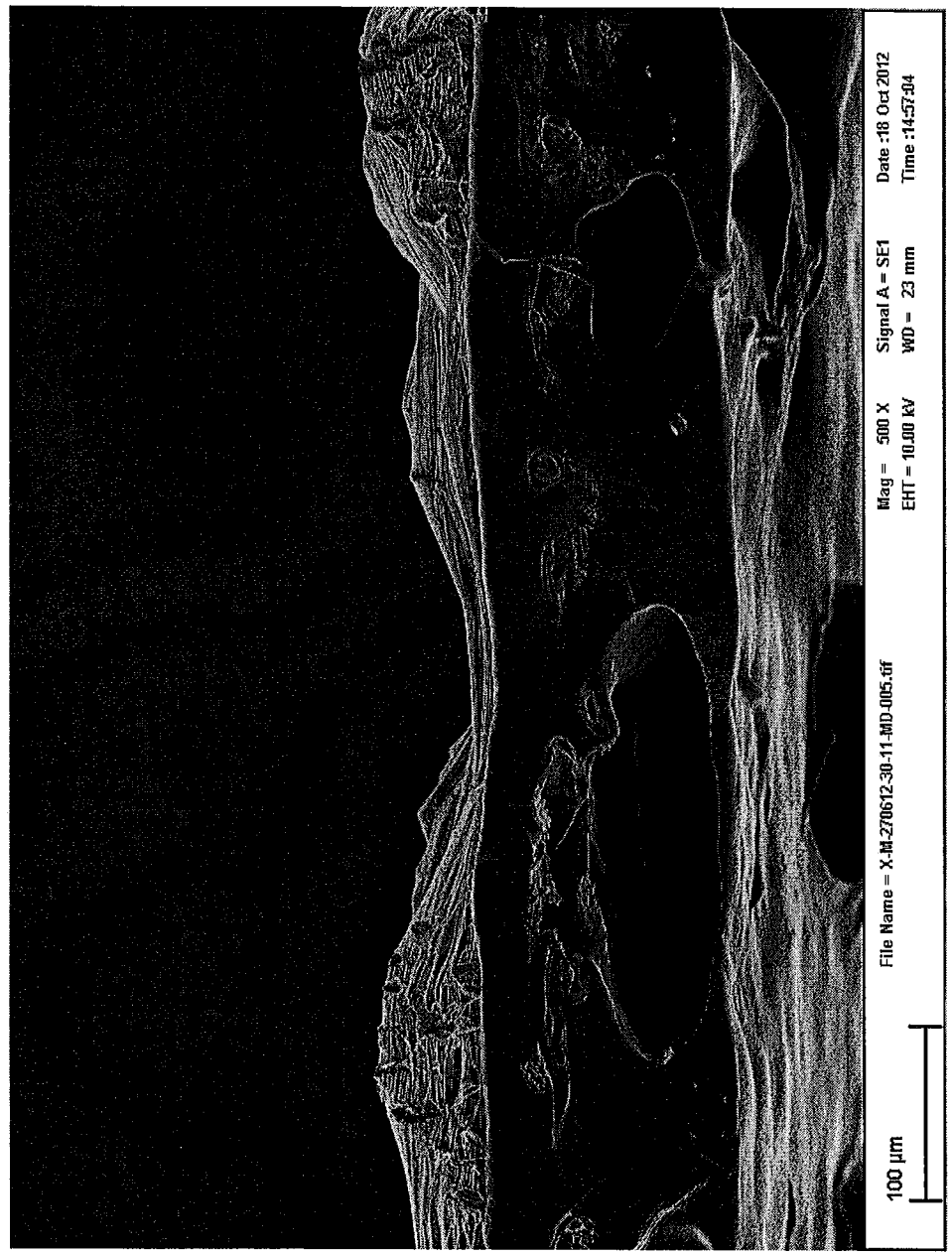
Fig. 4 (Tape T5)

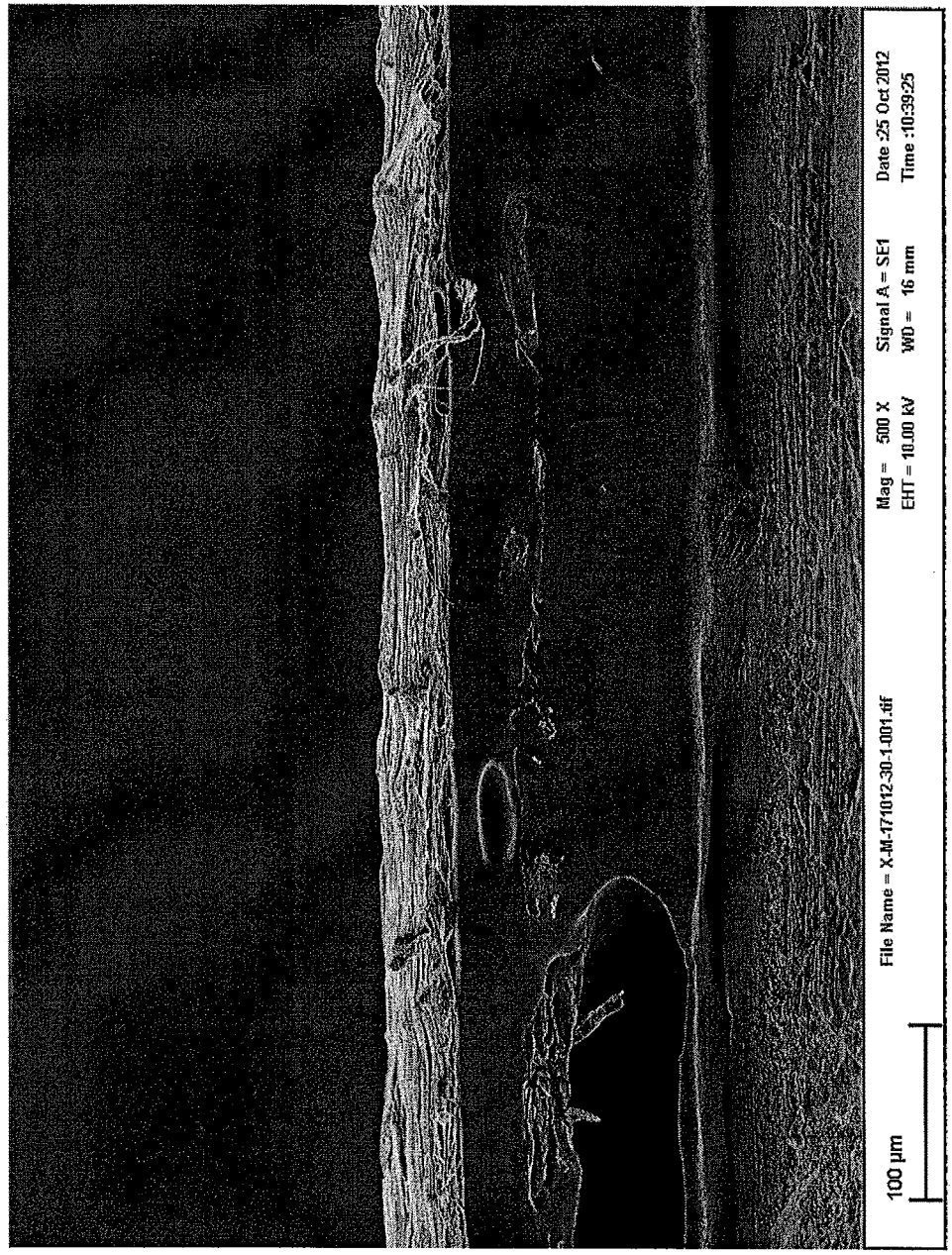
Fig. 5 (Tape T6)

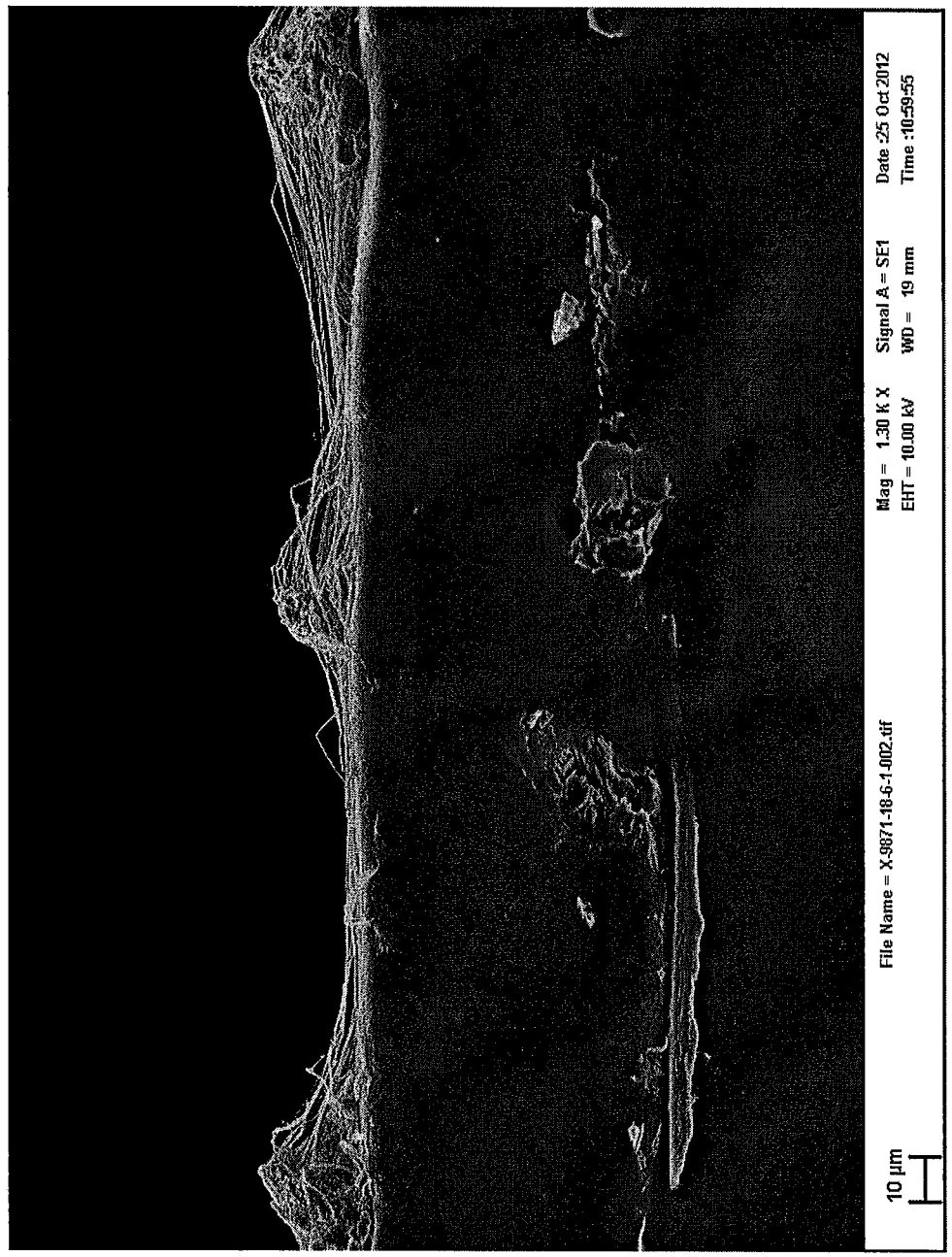
Fig. 6 (Membrane M2)

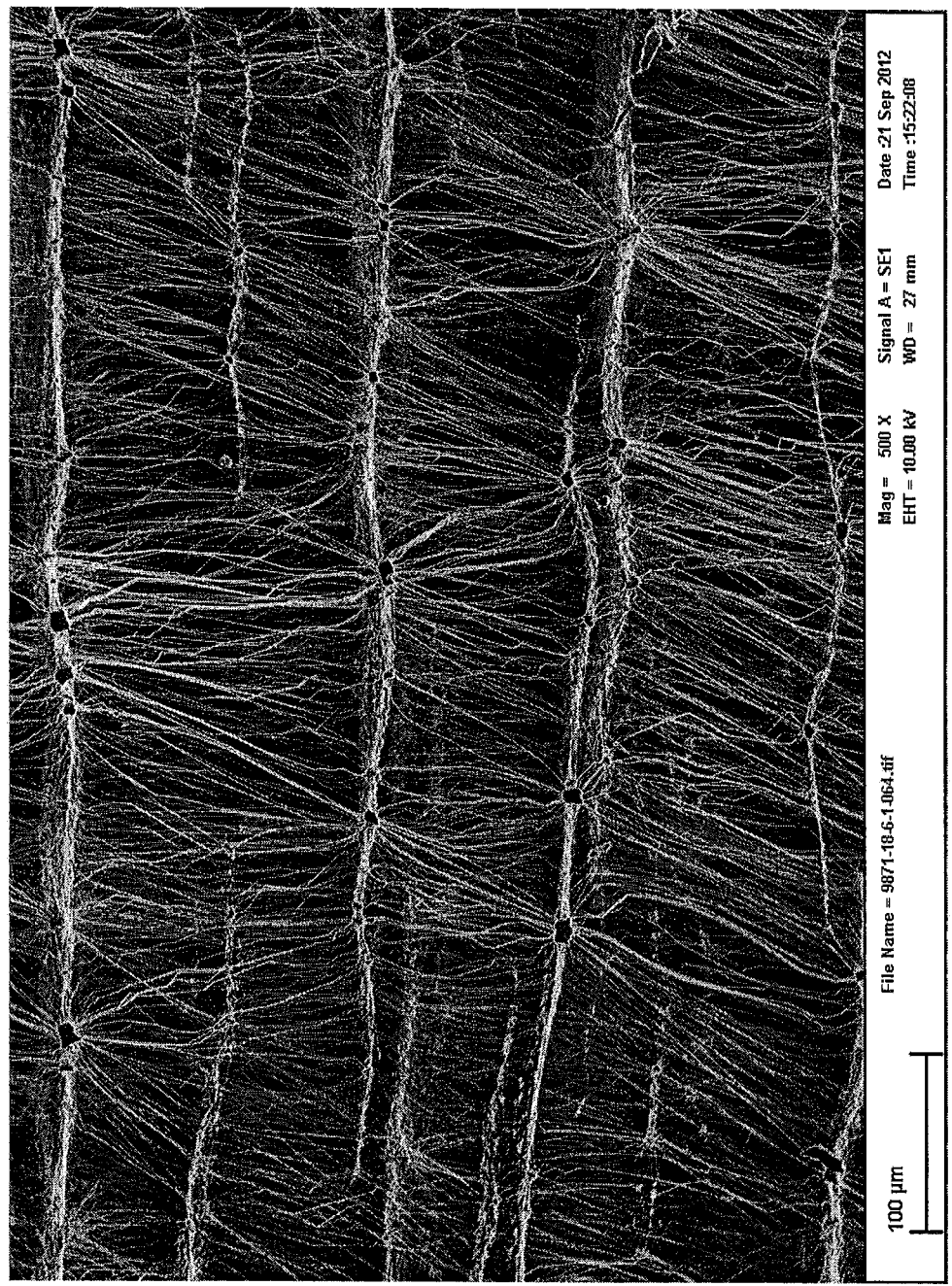
Fig. 7 (Membrane M2)

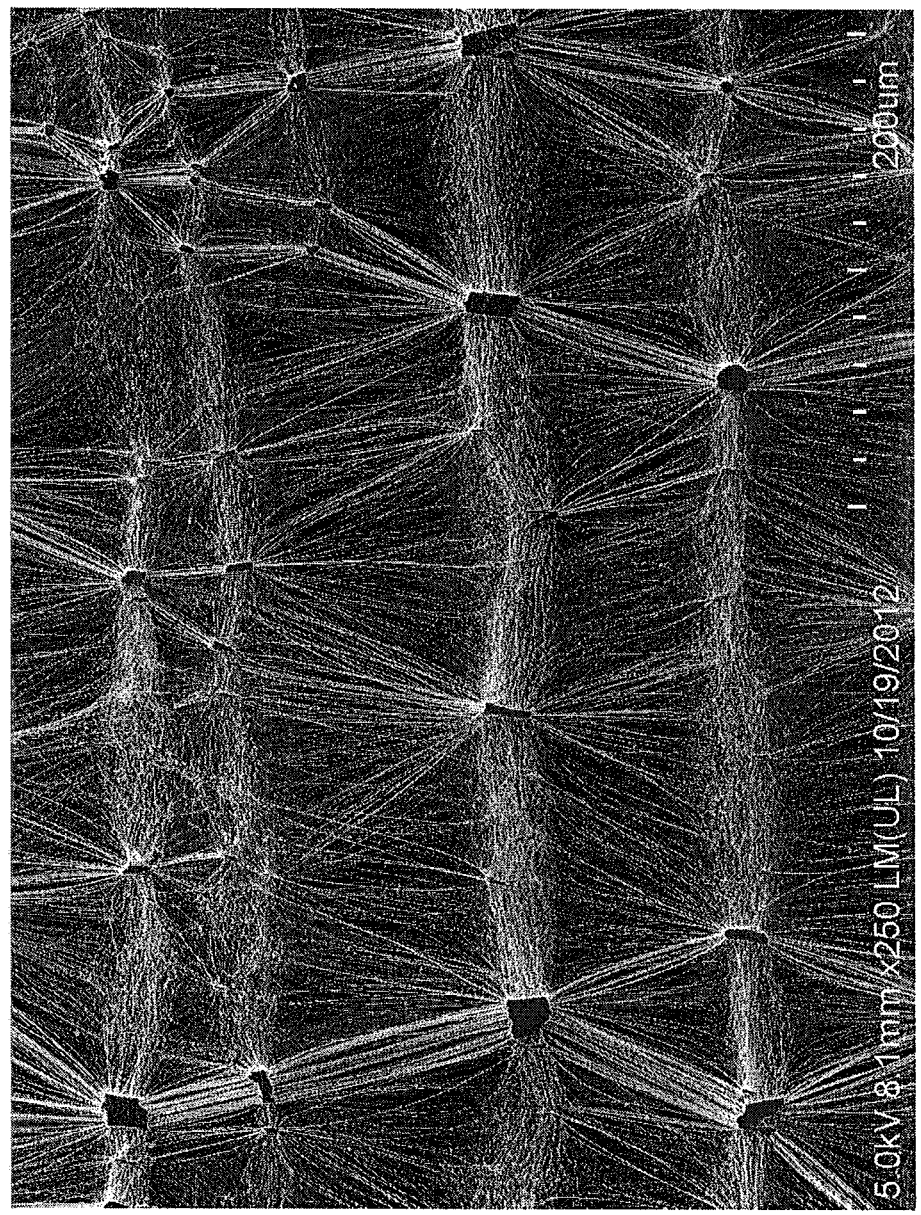
Fig. 8 (Membrane M3)

ns, tapes, and membranes, having a high
FLUOROPOLYMER ARTICLES HAVING A HIGH SURFACE ROUGHNESS AND HIGH COARSENESS The present invention relates to fluoropolymer articles, in particular fibers, tapes, and membranes, having a high coarseness and high surface roughness and to a process for the production of said fluoropolymer articles.

Fluoropolymer articles in general are known to have a low surface tension and low coefficient of friction. This usually results in a "slippery" perception by active touch or, with respect to fluoropolymer fibers, in a low grip or low knot retention. In addition, the rather smooth surface and the low surface energy make it difficult to homogeneously apply coatings to the surface, to grow tissue into the material, or to bond other materials to the fluoropolymer article.

Coarseness and surface roughness are related but not the same. As described in U.S. Pat. No. 4,598,011, the term 'coarse' is used to indicate that the nodes are larger, the fibrils are longer, and the effective size of the pores, i.e. channels through the material, is larger. The coarseness is therefore primarily influenced by the specific microstructure in the bulk. In contrast, the surface roughness is primarily due to the surface topography. As described by S. J. Ledermann, M. M. Taylor (1972), Perception & Psychophysics, Vol. 12 (5), p. 401-408, the perception of roughness by active touch is mainly dominated by two factors: the average distance between peaks (also denoted "average distance between nodes") and the peak-to-valley distance of the rough surface. Hence, in order for a surface to be rough a channel through the material is not mandatory as long as there is a deeping of a certain depth. Furthermore, in case of a high number of small channels, the porosity may be high, e.g. as determined by air permeability, but the surface has no roughness as the pores are too small.

It is, in principle, possible to add a particle onto the surface of the fluoropolymer in order to increase its surface roughness. However, usually the particulation is increased as the particles are rubbed off from the surface. Hence, increasing the surface roughness while concomitantly using a lower amount of particles (or even no particles at all) is desirable.

Thus, it is one object underlying the present invention to provide a fluoropolymer article having a unique microstructure with respect to the coarseness, i.e. higher coarseness and increased surface roughness and a method for the manufacturing of such an article.

A process leading to a relatively coarse microstructure was published in patents (see U.S. Pat. Nos. 4,598,011, 7,060,354, 5,708,044). The published processes miss at least one element out of the key elements of the inventive process technology, as described in detail below. Only if all three key elements are included in the process chain, the full range of the described unique properties can be achieved.

U.S. Pat. No. 4,598,011 describes that the key element for increasing coarseness is the degree of densification. Moreover, in U.S. Pat. No. 4,598,011 a coarseness index was used to describe the microstructure being defined as follows.

$$\text{Coarseness index} = \frac{\text{bulk density [g/cm}^3\text{]}}{\text{ethanol bubble point [PSI]}}$$

This coarseness index will be explained in more detail below.

U.S. Pat. No. 5,708,044 describes fluoropolymer articles having a high coarseness index in excess of the values stated in U.S. Pat. No. 4,598,011. The articles in U.S. Pat. No. 5,708,044 can only be obtained from processing a blend of fluoropolymer resins.

U.S. Pat. No. 5,814,405 describes membranes of polytetrafluoroethylene. However, the process of making these membranes requires an additional heat treatment (amorphous locking) step before stretching into the final form.

U.S. Pat. No. 7,445,843 describes the use of plasma treatment to increase the roughness of the surface.

U.S. Pat. No. 7,060,354 describes a dental floss having a comparably good surface roughness, peak-to-valley distance and low density.

However, the surface roughness and coarseness can still be improved. Furthermore, the surface roughness and coarseness should be increased without the need for additional treatment steps as required in some of the prior art.

The present invention is based on the surprising finding that a dramatic change in the microstructure with respect to coarseness and a dramatic increase in the surface roughness of fluoropolymer articles can be achieved if the article is produced from a paste-formed fluoropolymer product that has been formed at low temperatures, e.g. by extrusion and calendaring. This finding is in clear contrast to state-of-the art paste-processing technologies of fluoropolymers, e.g. as described in S. Ebnesajjad (2000), *Fluoroplastics*, Vol. Volume 1: Non-Melt Processible Fluoroplastics, Plastics Design Library.

The present invention therefore provides a process for producing a fluoropolymer article having a high surface roughness and high coarseness which comprises the following steps:
a) forming a paste comprising a fluoropolymer into a paste-formed fluoropolymer product at a temperature lower than 50° C.,
b) densifying the paste-formed product, and
c) stretching the densified paste-formed fluoropolymer product in at least one direction.

With this process it is possible to obtain fluoropolymer articles having a hitherto unknown high degree of coarseness and surface roughness. The process of the present invention produces porous fluoropolymer articles with coarseness indices far in excess of the values achieved by the prior art. Furthermore, also the peak-to-valley distance is far higher in the inventive materials leading to higher surface roughness.

Furthermore, the inventive process is not a priori restricted to a specific selection of fluoropolymer raw materials or blends as for example needed in the products in U.S. Pat. No. 5,708,044 or 5,814,405. The obtained fluoropolymer articles have a unique microstructure with respect to coarseness and surface roughness which results in a novel combination of properties like surface properties (roughness, fray resistance) and bulk properties (air flow, strength). Hence, for applications where increased grip, a perception of roughness by active touch, increased knot retention, increased fray resistance, improved wettability, increased wicking, or high air flow is of importance, just to list a few, the inventive technology offers solutions.

The article can be made into many different forms, e.g. fibers, sheets, tubes, rods, or any combination of these, to address the requirements of these systems. The term "fiber" is intended to denote all articles with an extension in one dimension being large compared to the extension in the other two dimensions, e.g. articles usually denoted as fibers, filaments or threads. The term "sheet" is intended to denote all articles with an extension in two dimension being large compared to the extension in the other, remaining dimension, e.g. articles usually denoted as sheets, tapes, films, or membranes. Each of these forms offers individual advantages against state-of-the-art fluoropolymer articles. For example, fibers with improved grip and cleaning sensation can be made, which can be of advantage when used as dental floss. Sheet-like articles, like membranes and tapes, offer a wide range from medium to very high air-flow in addition to the coarse micro-structure and perception of roughness. Further, the coarse microstructure and therefore improved wettability can ease the ability of these article to be coated or bonded to other materials like thermoplastic polymers.

The coarseness is defined herein in terms of the ethanol bubble point (EBP), which is a measure of the maximum pore size in the test specimen (see ASTM F316-80). Specifically, the EBP is the minimum pressure required to force air through an ethanol-saturated article of this invention. Raising the pressure slightly should produce steady streams of bubbles at many sites. Thus, the measurements are not biased by artifacts such as puncture holes in the material. Ethanol bubble point is inversely related to the maximum pore size; lower values of EBP indicate larger pores, or in the terminology of this application, coarser structure.

In order to provide a basis for comparison of coarseness, a "coarseness index" has been adopted from U.S. Pat. No. 4,598,011, which is defined as the bulk density of the stretched porous article divided by the EBP of that article:

$$\text{Coarseness index} = \frac{\text{bulk density [g/cm}^3\text{]}}{\text{ethanol bubble point [PSI]}}$$

Introducing the coarseness index provides a means of comparing prior art articles with articles of this invention. An increase in coarseness is indicated by an increase in the coarseness index.

No additives, such as fillers, or particles applied onto the surface are needed to obtain the microstructure and achieve the high surface roughness according to the present invention.

Hence, to make full use of the benefits of the present invention, in one embodiment the fluoropolymer article does not comprise particles on the surface or additives such as fillers, or, in a further embodiment, any further compound at all.

In addition, no treatment such as plasma treatment is needed. Hence, the process of the invention is preferably free of any treatment steps using plasma.

Paste Production

The fluoropolymer used to produce the fluoropolymer article according to the process of the invention may be partially fluorinated or fully fluorinated, i.e. perfluorinated. The term "fluoropolymer" also encompasses copolymers of fluorinated or perfluorinated monomers with comonomers not comprising fluorine, e.g. $C_2$ to $C_{20}$ alpha-olefins such as ethylene or propylene. Usually the total content of fluorinated and/or perfluorinated monomers is at least 75 mol %, preferably at least 85 mol %, more preferably at least 95 mol % and most preferably at least 99 mol % based on the fluoropolymer.

In one embodiment, the fluoropolymer comprises, or consists of, polytetrafluoroethylene (PTFE), a "modified PTFE", a TFE copolymer, a fluorothermoplastic or a fluoroelastomer or any combination of these materials. The term "modified PTFE" as used herein is intended to denote a type of tetrafluoroethylene copolymer in which in addition to tetrafluoroethylene monomer units further perfluorinated, fluorinated or non-fluorinated co-monomer units maybe present whereby the total amount of comonomers different from tetrafluoroethylene based on the total amount of the modified PTFE is not more than 0.5 mol % according to ISO 12086. The term "TFE copolymer" as used herein is intended to denote a type of tetrafluoroethylene copolymer in which in addition to tetrafluoroethylene monomer units further perfluorinated, fluorinated or non-fluorinated co-monomer units are present, for example in a range of from 0.005 to 15 mol %, preferably, 0.005 to 5.0 mol %.

In case the fluoropolymer comprises polytetrafluoroethylene (PTFE), a modified PTFE, a TFE copolymer, a fluorothermoplastic or a fluoroelastomer or any combination of these materials, the total amount of these materials is preferably at least 90 wt. %, more preferably at least 95 wt. % and most preferably at least 99 wt. % based on the fluoropolymer.

In a further embodiment, the fluoropolymer comprises, or consists of, PTFE, fluorinated copolymer and/or a modified PTFE and in still a further embodiment the fluoropolymer comprises, or consists of, PTFE and/or a modified PTFE, and in still a further embodiment, the fluoropolymer comprises, or consists of, PTFE.

Preferably, in the process according to the invention forming of the paste comprising a fluoropolymer into a paste-formed fluoropolymer product is done at a temperature equal to or lower than 45° C., more preferably at a temperature equal to or lower than 40° C., still more preferably at a temperature equal to or lower than 35° C., still more preferably at a temperature equal to or lower than 30° C., and most preferably at a temperature equal to or lower than 25° C.

Forming of the paste comprising a fluoropolymer into the paste-formed fluoropolymer product preferably comprises extrusion and/or calendaring of the paste. Such extrusion and calendaring processes are well-known in the art and inter alia described in S. Ebnesajjad (2000), *Fluoroplastics*, Vol. Volume 1: Non-Melt Processible Fluoroplastics, Plastics Design Library.

Preferably, the paste comprising the fluoropolymer further comprises a lubricant. Usual amounts of lubricant are known in the art, e.g. 10 vol. %-90 vol. % based on the total volume of the paste. Suitable lubricants, e.g. mineral spirits are also known from the art.

If present, the lubricant is preferably removed before the paste-formed fluoropolymer product is densified.

Densifying and Stretching

Subsequently the paste-formed product is densified, preferably by calendaring.

As already outlined above, the process comprises the step of stretching the densified and dry past-formed product in at least one direction. The step of stretching in at least one direction usually comprises one or more orientation steps.

In the present invention the term "stretch ratio" denotes the ratio between the length after stretching to the length before stretching.

In the present invention the term "average stretch rate" denotes the amount of relative change in length per pass divided by the duration of the stretching step.

Preferably the step of stretching of the densified paste-formed fluoropolymer product in at least one direction is performed over a hot plate.

At least one orientation step in the stretching of the densified paste-formed fluoropolymer product in at least one direction is preferably performed at a temperature of 250 to 370° C., more preferably performed at a temperature of 270 to 350° C., even more preferably performed at a temperature of 270 to 325° C. and most preferably performed at a temperature of 290 to 310° C.

Preferably, in at least one orientation step in the stretching of the densified paste-formed fluoropolymer product in at least one direction a stretch ratio of 5 to 500 is applied, more preferably stretch ratio of 8 to 100 is applied and most preferably a stretch ratio of 10 to 50 is applied.

In at least one orientation step in the stretching of the densified paste-formed fluoropolymer product in at least one direction preferably an average the stretch rate per pass is from 10 to 500%/s, more preferably from 10 to 100%/s.

The fluoropolymer after stretching may or may not be subjected to a sintering or annealing treatment.

In one embodiment of the process, at least one orientation step in the stretching of the densified paste-formed fluoropolymer product in at least one direction is performed by stretching the fluoropolymer precursor with a stretching rate of 5%/s or more, in a further embodiment of 10%/s or more, in a still a further embodiment of 30%/s or more, and in still a further embodiment of 70%/s or more.

In another embodiment, especially applicable for the case of the fluoropolymer being in the form of fibers of the process at least two orientation steps are carried out, more preferably two orientation steps are subsequently carried out in the same direction. In this embodiment the second orientation step in the stretching of the densified paste-formed fluoropolymer product in at least one direction is performed by stretching the fluoropolymer precursor at a temperature of from 280 to 400° C., preferably at a temperature of from 290 to 380° C., and more preferably at temperature of from 320 to 380° C.

Stretching may also be performed in more than one direction, e.g. in case of the fluoropolymer being in the form of sheets, such as membranes. Thus the step of stretching of the densified paste-formed fluoropolymer product in at least one direction may comprise one, two or more orientation steps, usually not more than two orientation steps. In case of two or more orientation steps these orientation steps maybe carried out in different directions. For example in case of membranes, usually the stretching is performed in at least two directions.

In the case of sheets as defined above and concomitantly in case the step of stretching of the densified paste-formed fluoropolymer product in at least one direction comprises two orientation steps, these the directions of the orientation steps are usually perpendicular to each other, more preferably, the two directions of the orientation steps are the machine direction and the direction perpendicular thereto, usually also denoted transverse direction.

In case the step of stretching of the densified paste-formed fluoropolymer product in at least one direction comprises two or more orientation steps, the orientation steps may be carried out subsequently or simultaneously.

In a preferred embodiment in case the step of stretching of the densified paste-formed fluoropolymer product in at least one direction comprises two orientation steps and the two directions of the orientation steps are the machine direction and the direction perpendicular thereto (=transverse direction) and the steps are carried out subsequently, preferably, the orientation step in machine direction is carried out prior to the orientation step in transverse direction.

In case two or more orientation step are present in the step of stretching of the densified paste-formed fluoropolymer product in at least one direction all steps maybe carried out under the conditions described above. This means that, in such a case the conditions of each orientation step are selected to be within the above ranges. However, in such a case the conditions of each orientation step may be independently selected within the above ranges.

Of course, as will be readily appreciated, in case two or more orientation steps are carried out simultaneously the temperature of these orientation steps is the same.

In the following a preferred embodiment of the step of stretching of the densified paste-formed fluoropolymer product in at least one direction in case of fibers is described.

In this embodiment, at least one, preferably at least two orientation steps are carried out, more preferably two orientation steps are carried out. In case of fibers all orientation steps are carried out in the direction of the fiber.

The first orientation step, is preferably carried out at a temperature of 280 to 340° C., more preferably 290° C. to 320° C.

Preferably, in the first orientation step the stretch ratio is within the range of 5 to 50, more preferably 10 to 50.

In the first orientation step the stretch rate is preferably up to 200%/s, more preferably up to 100%/s and most preferably up to 90%/s. Usually in the first orientation step the stretch rate is at least 10%/s.

The second orientation step, is preferably carried out at a temperature of 280 to 400° C., more preferably at a temperature of 290° C. to 380° C. and most preferably at a temperature of 320 to 380° C.

Preferably, in the second orientation step the stretch ratio is within the range of 1.5 to 10, more preferably 1.5 to 5.

In the second orientation step the stretch rate is preferably within the range of 5 to 50%/s, more preferably 10 to 30%/s.

The second orientation step is subsequent to the first orientation step. Hence, in case only one orientation step is present, the first orientation step is present.

In the following a preferred embodiment of the step of stretching of the densified paste-formed fluoropolymer product in at least one direction in case of tapes is described.

In this embodiment, usually only one orientation steps is carried out, preferably, this step is carried out in machine direction.

The orientation step, is preferably carried out at a temperature of 280 to 340° C., more preferably 290° C. to 320° C.

Preferably, in the orientation step the stretch ratio is within the range of 5 to 50, more preferably 8 to 35.

In the orientation step the stretch rate is preferably within the range of 10 to 200%/s, more preferably 15 to 100%/s.

In the following a preferred embodiment of the step of stretching of the densified paste-formed fluoropolymer product in at least one direction in case of membranes is described.

In this embodiment, at least two orientation steps are carried out, preferably two orientation steps are carried out. These orientation steps are usually carried out in machine direction and transverse direction, preferably, the orientation step in machine direction is carried out prior to the orientation step in transverse direction.

The orientation step in machine direction, is preferably carried out at a temperature of 280 to 340° C., more preferably 290° C. to 320° C.

Preferably, in the orientation step in machine direction the stretch ratio is within the range of 5 to 30, more preferably 5 to 20.

In the orientation step in machine direction the stretch rate is preferably within the range of 10 to 100%/s, more preferably 15 to 50%/s.

The orientation step in transverse direction, is preferably carried out at a temperature of 280 to 340° C., more preferably 290° C. to 320° C.

Preferably, in the orientation step in transverse direction the stretch ratio is within the range of 2 to 25, more preferably 5 to 15.

In the orientation step in transverse direction the stretch rate is preferably within the range of 50 to 1000%/s, more preferably 75 to 750%/s.

In case of tubes the stretching step c) comprises or consists of, the step of expansion of the tube as, inter alia described in U.S. Pat. No. 3,953,566, e.g. example 8. In such an expansion step, the diameter of the tube after expansion is usually at least 2 times the diameter prior to expansion.

Unless otherwise indicated to the contrary, In the following preferred features of all embodiments of the process of the present invention are described.

Furthermore, the process according to the invention is for the manufacture of the paste-formed fluoropolymer product in any of the above described embodiments.

The densification of the paste-formed fluoropolymer product can be performed through the use of presses, dies, or calendaring machines. The use of a calendaring machine to densify the dry product enables the manufacture of long lengths of film.

The highest densifications produce the most dramatic effect. In order to achieve the highest densification, it is necessary that the densified article be subjected to compressive forces until all void closure is achieved. At a fixed temperature, increased compressive force accelerates the rate of densification, as would be expected.

Although a densification at elevated temperatures, e.g. up to 345° C. is possible, the densification is usually effected at a temperature below 300° C.

Preferably, in the process according to the invention the paste-formed fluoropolymer product in the densification step is densified to a porosity of less than 30%, more preferably of less than 20%, still more preferably of less than 10%, and most preferably of less than 5%.

In a preferred embodiment of the process according to the invention the fluoropolymer is PTFE and the paste-formed fluoropolymer product in the densification step is densified to a bulk density of at least 1.6 g/cm$^3$, more preferably to a bulk density of at least 1.8 g/cm$^3$, still more preferably to a bulk density of at least 2.1 g/cm$^3$ and most preferably to a bulk density of at least 2.2 g/cm$^3$.

The present invention furthermore relates to a fluoropolymer article obtainable by a process according to any of the above described embodiments.

The fluoropolymer article preferably has a surface roughness expressed as a peak-to-valley distance (Rt) greater than 10 micrometer, more preferably greater than 15 micrometer.

Preferably the fluoropolymer article has a root-mean-square roughness (Rq) greater than 1.1, more preferably greater than 1.5 micrometer.

The fluoropolymer article further preferably has an average distance between nodes greater 50 micrometer.

Preferably the fluoropolymer article has an average surface roughness greater than 3 micrometer.

Preferably the fluoropolymer article has a coarseness index of at least 0.25 g/cm$^3$/PSI.

Preferred embodiments of the fluoropolymer article are fibers, e.g. dental floss, tapes, membranes, rods or tubes.

Still further, the invention relates to a fluoropolymer article having a surface roughness expressed as a peak-to-valley distance (Rt) greater than 10 micrometer, preferably greater than 15 micrometer and most preferably greater than 20 micrometer;

an average distance between nodes of greater 50 micrometer; and an average surface roughness greater than 3 micrometer.

Preferably the fluoropolymer article has a root-mean-square roughness (Rq) greater than 1.1, more preferably greater than 1.5 micrometer.

Furthermore, preferably the fluoropolymer article has a coarseness index of at least 0.25 g/cm$^3$/PSI. In one embodiment the coarseness index maybe 0.75 g/cm$^3$/PSI or more and in another embodiment the coarseness index maybe 2.0 g/cm$^3$/PSI Preferred embodiments of the fluoropolymer article are fibers, e.g. dental floss, tapes, membranes, rods or tubes.

The fluoropolymer article according to the invention in any of its embodiments described herein is preferably produced according to the process of the invention in any of its embodiments described herein.

Still further, the invention relates to a fiber comprising, or consisting of, a fluoropolymer having a surface roughness expressed as a peak to valley distance (Rt) greater than 10 micrometer, preferably greater than 15 micrometer and most preferably greater than 20 micrometer and/or an average surface roughness (Ra) greater than 1.5 micrometer, preferably, to a fiber comprising, or consisting of, a fluoropolymer having.

a surface roughness expressed as a peak-to-valley distance (Rt) greater than 10 micrometer, more preferably greater than 15 micrometer and most preferably greater than 20 micrometer;

an average surface roughness (Ra) greater than 1.5 micrometer; and a root-mean-square roughness (Rq) greater than 1.5 micrometer; and/or an average distance between nodes of at least 75 micrometer, preferably of at least 100 micrometer; and/or In one embodiment the an average surface roughness (Ra) is at least 5 micrometer, the root-mean-square roughness (Rq) is at least 6 micrometer and the an average distance between nodes is at least 300 micrometer.

The fluoropolymer fiber is comprising, or consisting of usually has a Titer of 700 denier or more and/or a Tenacity of 2.0 [gf/denier] or more.

Furthermore, the fluoropolymer fiber is comprising, or consisting of preferably has a wicking height of at least 35 mm after 30 minutes.

The fibers according to the invention in any of its embodiments described herein are preferably produced according to the process of the invention in any of its embodiments described herein.

Fibers comprising, or consisting of, a fluoropolymer having such high surface roughness have not been known in the art and allow for new applications of such fibers, for example, as dental floss.

Thus, the present invention also relates to a dental floss comprising, or consisting of, such fibers and to the use of such fibers in a dental floss.

The present invention furthermore relates to a tape comprising or consisting of, a fluoropolymer having a surface roughness expressed as a peak-to-valley distance (Rt) greater than 10 micrometer, more preferably greater than 15 micrometer and most preferably greater than 20 micrometer;

a root-mean-square roughness (Rq) greater than 4 micrometer;

an average distance between nodes of at least 100 micrometer; and/or an average surface roughness (Ra) of at least 3 micrometer;

Preferably the fluoropolymer the tape is comprising or consisting of, has a coarseness index of at least 0.25 g/cm$^3$/PSI.

In one embodiment the coarseness index is 1.5 g/cm$^3$/PSI or higher, the average surface roughness (Ra) is at least 5 micrometer and the peak-to-valley distance (Rt) is at least 70 micrometer.

The fluoropolymer the tape is comprising or consisting of, preferably has a ballburst strength of at least 3 lbs.

Preferably, the fluoropolymer the tape is comprising or consisting of, has an air permeability of at least 1.5 ft$^3$/ft$^2$/min, preferably at least 3.0 ft$^3$/ft$^2$/min.

The tapes according to the invention in any of its embodiments described herein are preferably produced according to the process of the invention in any of its embodiments described herein.

The present invention furthermore relates to a membrane comprising, or consisting of, a fluoropolymer having a coarseness index ρ/EBP of at least 0.3, an air permeability of 15 ft$^3$/ft$^2$/min or higher and a node aspect ratio of below 25, more preferably below 10, and most preferably below 3.

Preferably the fluoropolymer the membrane is comprising, or consisting of has a coarseness index of at least 0.5 g/cm$^3$/PSI.

The fluoropolymer the membrane is comprising, or consisting of, preferably an air permeability of 50 ft$^3$/ft$^2$/min or higher.

Furthermore, the fluoropolymer the membrane is comprising, or consisting of preferably has a ballburst strength of at least 1.25 lbs.

The membranes according to the invention in any of its embodiments described herein are preferably produced according to the process of the invention in any of its embodiments described herein.

The present invention also relates to an article comprising the membrane in any of its embodiments as described herein.

REFERENCES CITED

S. J. Ledermann, M. M. Taylor (1972), Perception & Psychophysics, Vol. 12 (5), p. 401-408

S. Ebnesajjad (2000), *Fluoroplastics*, Vol. Volume 1: Non-Melt Processible Fluoroplastics, Plastics Design Library.

U.S. Pat. No. 4,598,011
U.S. Pat. No. 7,060,354
U.S. Pat. No. 5,708,044
U.S. Pat. No. 7,445,843
U.S. Pat. No. 5,814,405

DESCRIPTION OF THE FIGURES

FIG. 1 shows the scanning electron micrograph of the surface of fiber F3. The machine direction is from the bottom of the figure to the top.

FIG. 2 shows the scanning electron micrograph (SEM top view) of the surface of fiber F1. The machine direction is from the bottom of the figure to the top.

FIG. 3 shows the scanning electron micrograph (SEM top view) of the surface of Tape T5. The machine direction is from the bottom of the figure to the top.

FIG. 4 shows the scanning electron micrograph (SEM cross section) of Tape T5. The machine direction is from the left of the figure to the right.

FIG. 5 shows the scanning electron micrograph (SEM cross section) of Tape T6. The machine direction is from the left of the figure to the right.

FIG. 6 shows the scanning electron micrograph (SEM cross section) of membrane M2. The machine direction is from the left of the figure to the right.

FIG. 7 shows the scanning electron micrograph (top view) of membrane M2. The machine direction is from the bottom of the figure to the top.

FIG. 8 shows the scanning electron micrograph (top view) of membrane M3. The machine direction is from the bottom of the figure to the top.

The present invention will be further illustrated by the examples described below.

EXAMPLES

1) Measurement Methods a) Surface topography

The surface topography of the examples was characterized by the height of peaks generated by nodal structures, the peak to valley distance, and the average distance between them preferably projected onto the direction of the first stretching step (machine direction). The data were generated from scanning electron micrographs of the surface and the cross-section parallel to the machine direction.

In addition, the surface roughness and peak to valley distance (Rt) of fibers and tapes were characterized using a Zygo NewView™ 7200 3D optical surface profiler. A cylinder background form removal was applied to all samples to correct for the curvature. Subsequently, a high FFT frequency filter at 20 micrometer wavelength was applied to minimize noise. No filter trim was used to preserve edge data. Data analysis was conducted using MetroPro 8.3.5 from Zygo.

The surface roughness and peak to valley distance are defined as follows:

Ra: Arithmetical mean deviation. The average roughness or deviation of all points from a plane fit to the test part surface.

Rq: Rq is the root mean square parameter corresponding to Ra.

Rt: Maximum peak-to-valley height. The absolute value between the highest and lowest peaks.

b) Microstructure

The aspect ratio of the surface of the nodal areas was determined from scanning electron micrographs. At least five such measurements were taken of representative nodes.

The average distance between nodes in machine direction (MD) has been determined from the average length of lines oriented in machine direction and connecting nodes. At least ten such measurements were taken of representative nodes.

c) Air permeability was measured according to ASTM D 737 of at least three samples. At least five such measurements were taken.

d) Ethanol Bubble Point (EBP) was determined according to ASTM F360-80. At least three such measurements were taken.

e) Mechanical testing

Tenacity was determined according to EN ISO 2062.

Ball burst was measured using a Chatillon TCD200 digital force tester. Burst strength measures the relative strength of a sample by determining the maximum load at break. A single layer of the sample is challenged with a 25 mm diameter ball while being clamped and restrained in a ring of xmm inside diameter. The sample is placed taut in the ring and pressure applied against it by the steel ball of the ball burst probe approaching the center of the sample at a constant speed of 10 inch/minute. Maximum load is recorded as "ball burst" in pounds. At least three such measurements were taken.

f) Vertical wicking test

The ability for the present invention to move liquid moisture was measured using the following test method. Two hundred ml of isopropanol alcohol (IPA) USP HPLC grade was placed in a clean and dry 500 ml Erlenmeyer flask. The Erlenmeyer flask rested on top a level lab bench surface such that the inside of the flask is easily observed. A piece of black construction paper the size of 8½×11 inch (216×279 mm) was placed behind the flask to aid in the observation of the wicking IPA media advancing up the test filament. A 250 mm long stainless steel ruler having the precision of 0.5 mm was affixed vertically against the back inside wall of the Erlenmeyer flask with double-sided adhesive tape such that the distal end starting at 0 mm rested on the floor of the flask. A length of dry filament approximately 147 mm was cut randomly from a spool of test filament candidate. A 1.67 gram Rubber-Grip™ lead fishing (sinker) weight was affixed to one distal end of the filament and the second distal end was affixed to a wooden dowel/stick. The wooden dowel has a round cross-section approximately 2 mm diameter by 100 mm long. The overall length of the secured test filament is such that when the distal end containing the fishing weight is lowered inside the Erlenmeyer flask, at least 1 mm of filament and the fishing weight are totally submerged in the IPA with no slack in the filament as the wooden dowel/stick rest on top of the upper lip of the Erlenmeyer flask. Erlenmeyer contains 250 ml IPA before the filament is lowered inside.

Once the dry test filament having the fishing weight affixed, it is lowered inside the Erlenmeyer flask, is submerged and the dowel stick is resting on the top lip of the flask, an electronic stopwatch (precision ±0.1 seconds) was started. Observations of the IPA media wicking up the filament are made at certain time intervals, 1, 6, and 16 minutes.

At least 5 wicking tests are performed for each test filament candidate. The graph below shows the wicking height vs. time for three examples of the present invention compared to commercially available Comfort Plus Dental Floss from the Procter and Gamble Company which had its waxed coating removed using five 5-minute rinses of hexane at 40° C. followed by three rinses of de-ionized water at ambient temperature and then dried at ambient temperature. No wicking was observed to occur within the 16 minute test duration using another commercially available PTFE dental floss and is thus not plotted in the graph. This floss is Original GLIDE® Dental Floss from the Procter and Gamble Company. The Original GLIDE® Dental Floss had its waxed coating removed prior to testing using five 5-minute rinses of hexane at 40° C. followed by three rinses of de-ionized water at ambient temperature and then dried at ambient temperature. After the test is completed, the filament is removed and the IPA is drained from the flask. The flask is cleaned and dried. At least three such measurements were taken.

f) Coarseness index

The coarseness index is defined herein as the bulk density of the stretched porous article divided by the ethanol bubble point of that article.

$$\text{Coarseness index} = \frac{\text{bulk density [g/cm}^3\text{]}}{\text{ethanol bubble point [PSI]}}$$

g) Conversion factors to SI units:
1 lbf=4.4482 N
1 denier=1 g per 9000 m length=0.1111 tex
1 tex=1 g per 1000 m length
1 gF/denier=0.8829 N/tex
1 ft$^3$/ft$^2$/min=0.00508 m$^3$/m$^2$/s
1 PSI=6894.757 Pa h) Bulk Density The bulk density is the ratio between the mass of the example and its volume as determined by the measured dimensions.

i) Porosity

Porosity was determined from the ratio between the actual bulk density $\rho_{actual}$ of the porous material and the highest density $\rho_{max}$ of the non-porous material according to $$\text{Porosity} = 1 - \frac{\rho_{actual}}{\rho_{max}}$$

2) Preparation of Fluoropolymer Articles

Following the procedures disclosed in U.S. Pat. Nos. 3,953,566, 3,962,153, and 4,064,214 a precursor tape was prepared in the following manner:

A fine powder PTFE resin was mixed with mineral spirit (24.3 wt %) to form a paste and extruded through a die to form a wet tape of 0.775 mm thickness at 25° C. Subsequently, the wet tape was rolled down at 25° C., and than dried at 185° C. to remove the mineral spirit. The dry tape had a final thickness of 0.152 mm.

To demonstrate the effect of the low process temperature when making the paste-formed intermediate product, another comparative dry precursor tape was made using the same recipe as above, but increasing the extrusion and calendaring temperatures to 50° C. The final dimensions of the comparative dry tape were similar to the dimensions of the tape described in the section above, which precursor has been used for which example is indicated below.

Subsequently the dry tapes were densified to a bulk density of 2.2 g/cm$^3$, i.e. porosity of <5% assuming $\rho_{max}$=2.3 g/cm$^3$, by passing them between two hard steel rolls at a line speed of 10 m/min and a line pressure of 25 kN.

The densified precursor tapes can be cut and/or stretched into any desired shape according to the inventive process as follows.

Fibers

Prior to any stretching step the densified precursor tape described above was slit to 17.75 mm widths by passing it between a set of gapped blades to serve as precursor fibers.

The precursor fibers were stretched over hot plates at 300° C. to 320° C. in a first pass, at 360° C. in a second pass, and finally heated to 425° C. without stretching for at least 5 seconds to form a fiber. The total stretch ratio was 50:1. The stretch ratios, average stretch rates, and temperatures of the individual passes were varied as shown in Table 1 to produce fibers (inventive examples ID F1-F3) with different degrees of coarseness and surface roughness from low to high. Comparative samples F4 and F5 denote two commercially available floss products with trade names Glide® original floss and Glide® comfort plus, respectively.

The fibers were measured to characterize the mechanical properties, surface structure, and wicking behavior by the methods described hereinabove. The results are shown in Table 2.

TABLE 1

Process parameters - fibers

| Sample ID | Pass 1 Stretch ratio | Pass 1 Average stretch rate [%/s] | Pass 1 Temperature [° C.] | Pass 2 Stretch ratio | Pass 2 Average stretch rate [%/s] | Pass 2 Temperature [° C.] |
| --- | --- | --- | --- | --- | --- | --- |
| F1 | 25 | 195.1 | 320 | 2 | 13.1 | 360 |
| F2 | 15 | 78.9 | 310 | 3.34 | 24.6 | 360 |
| F3 | 15 | 39.5 | 300 | 3.34 | 12.3 | 360 |

TABLE 2

Characterization - fibers

| Sample ID | Titer [denier] | Tenacity [gF/denier] | Wicking height after 30 minutes [mm] | Average surface roughness (Ra) [micrometer] | Root Mean Square surface roughness (Rq) [micrometer] | Peak to valley (Rt) [micrometer] | Average distance between nodes in MD [micrometer] |
| --- | --- | --- | --- | --- | --- | --- | --- |
| F1 | 803 | 3.18 | 41 | 0.88 | 1.12 | 23.15 | 70 |
| F2 | 1131 | 3.09 | 44 | 1.53 | 1.95 | 31.36 | 117 |
| F3 | 797 | 2.23 | 71 | 6.17 | 7.58 | 78.80 | 454 |
| F4 | 1247 | 4.04 | 0 | n.a. | n.a. | n.a. | n.a. |
| F5 | 1000 | 2.86 | 30 | 0.77 | 0.96 | 15.37 | n.a. |

Tapes

The precursor tape as described above was stretched over hot plates in a single pass at 300° C. (inventive examples ID T1, T4 and T5). According to the procedure described in U.S. Pat. No. 3,953,566, the stretched tape was subject to an additional heat treatment or sintering step by passing it over hot rolls at 360° C. for 5 seconds making example T2.

The stretch ratios, stretch rates, and temperatures were varied as shown in Table 3 to produce tapes with different degrees of surface roughness.

A comparative precursor tape, which has been extruded and calendared at 50° C., was stretched over hot plates in a single pass at 300° C. From this comparative precursor tape examples T3, and T6 were produced using the same stretch ratios, stretch rates, and temperatures as used for making examples T1 and T5, respectively. Accordingly, the coarseness and surface roughness of samples T3, and T6 drops significantly as shown in FIGS. 4 and 5.

The tapes were measured to characterize the mechanical properties, air permeability, bubble point, water entry pressure and surface structure by the methods described hereinabove. The results are shown in Table 4 and 5. Please note, that peak-to-valley values marked by a star were estimated from the largest peak-to-valley distance determined from SEM cross-sections along a single cut in machine direction. Due to the limited amount of available data, these values present only a lower limit.

TABLE 3

Process parameter - tapes

| Sample ID | Stretch ratio | Estimated average stretch rate [%/s] | Temperature [° C.] | Sintering |
| --- | --- | --- | --- | --- |
| T1 | 10 | 17.8 | 300 | no |
| T2 | 10 | 17.8 | 300 | yes |
| T3 | 10 | 17.8 | 300 | no |
| T4 | 20 | 49.8 | 300 | no |
| T5 | 30 | 90.4 | 300 | no |
| T6 | 30 | 90.4 | 300 | no |

TABLE 4

Characterization - tapes

| Sample ID | Area weight [g/m²] | Thickness [10⁻⁶ m] | Ballburst strength [lbs] | Airflow [ft³/ft²/min] | Ballburst * Airflow [lbs * ft³/ft²/min] | EBP [PSI] |
| --- | --- | --- | --- | --- | --- | --- |
| T1 | 22.8 | 88 | 5.1 | 1.8 | 9.05 | 0.87 |
| T2 | 24.8 | 91 | 8.5 | 4.0 | 33.88 | 1.25 |
| T3 | 23.1 | 87 | 12.2 | 0.7 | 8.07 | 1.95 |
| T4 | 11.5 | 81 | 3.9 | 9.0 | 34.73 | 0.22 |
| T5 | 7.8 | 53 | 3.2 | 13.3 | 42.37 | 0.05 |
| T6 | 9.0 | 35 | 7.9 | 0.9 | 7.24 | 1.55 |

TABLE 5

Characterization - tapes

| Sample ID | Coarseness index [g/cm³/PSI] | Average surface roughness (Ra) [micrometer] | Root Mean Square surface roughness (Rq) [micrometer] | Peak to valley (Rt) [micrometer] | Average distance between nodes in MD [micrometer] |
|---|---|---|---|---|---|
| T1 | 0.30 | 3.22 | 4.30 | 53.59 | 130 |
| T2 | 0.27 | n.a. | n.a. | n.a. | 144 |
| T3 | 0.14 | n.a. | n.a. | >4.9* | 67 |
| T4 | 0.64 | 7.12 | 9.37 | 111.91 | 222 |
| T5 | 2.79 | 5.72 | 7.40 | 73.7 | 309 |
| T6 | 0.16 | n.a. | n.a. | >5.3* | 149 |

Membranes

The densified precursor tape as described above was stretched over hot plates in a single pass in one machine direction (designated as x) at 300° C., and stretched along a direction perpendicular (transverse direction) to the first pass (designated y) at 300° C. in a second pass. According to the procedure described in U.S. Pat. No. 3,953,566, one sample of each biaxially stretched membrane was subject to an additional heat treatment or sintering step by subjecting to sample to hot circulated air at 375° C. for 5 seconds.

The stretch ratios, average engineering stretch rates, and temperatures of the individual passes were varied as shown in Table 6 to produce membranes (inventive examples ID M1-M3) with different degrees of coarseness, surface roughness, and air permeability The membranes were measured to characterize the mechanical properties, air permeability, bubble point, water entry pressure and surface structure by the methods described hereinabove. The results are shown in Table 7 and 8. Please note, that peak-to-valley values marked by a star were estimated from the largest peak-to-valley distance determined from SEM cross-sections along a single cut in machine direction. Due to the limited amount of available data, these values present only a lower limit.

TABLE 6

Process parameter - membranes

| Sample ID | Pass 1 - x Stretch ratio | Pass 1 -x Estimated average stretch rate [%/s] | Pass 1 - x Temperature [° C.] | Pass 2 - y Stretch ratio | Pass 2 -y average stretch rate [%/s] | Pass 2 - y Temperature [° C.] | Sintering |
|---|---|---|---|---|---|---|---|
| M1 | 16 | 36.8 | 300 | 8 | 700 | 300 | no |
| M2 | 16 | 36.8 | 300 | 8 | 700 | 300 | yes |
| M3 | 8 | 21.4 | 300 | 8 | 700 | 300 | no |

TABLE 7

Characterization - membranes

| Sample ID | Area weight [g/m²] | Thickness [micrometer] | Ballburst [lbs] | Airflow [ft³/ft²/min] | Ballburst * Airflow [lbs * ft³/ft²/min] | EBP [PSI] |
|---|---|---|---|---|---|---|
| M1 | 0.18 | 6.1 | 1.517 | 67.1 | 101.79 | 0.5 |
| M2 | 0.19 | 5.2 | 1.645 | 83.7 | 137.69 | 0.36 |
| M3 | 0.43 | 6.3 | 2.671 | 15.3 | 40.87 | 1.08 |

TABLE 8

Characterization - membranes

| Sample ID | Coarseness index [g/cm³/PSI] | Average distance between nodes in MD [micrometer] | Average node aspect ratio | Average Node area [micrometer²] | Peak to valley [micrometer] |
|---|---|---|---|---|---|
| M1 | 0.59 | 156.45 | 1.53 | 67 | >27.81* |
| M2 | 1.01 | 148.38 | 1.22 | 90 | >19.5* |
| M3 | 0.64 | 86.91 | 1.54 | 124 | >13.7* |

The invention claimed is:

1. A fluoropolymer article comprising:
   a fluoropolymer fiber having a surface roughness expressed as a peak-to-valley distance (Rt) of greater than 10 micrometers;
   an average distance between nodes of greater than 50 micrometers;
   an average surface roughness (Ra) of greater than 3 micrometers; and
   a coarseness index of at least 025 g/cm³/psi.

2. The article of claim 1, wherein said fiber has a porosity of less than 30%.

3. An article comprising:
   a fluoropolymer fiber having a surface roughness expressed as a peak-to-valley distance (Rt) of greater than 10 micrometers an average surface roughness (Ra) of greater than 3.0 micrometers and an average distance between nodes of greater than 50 micrometers,
   wherein said fiber has an extension in one dimension that is greater than the extension in other dimensions.

4. The article of claim 3, wherein said fiber has a tenacity of 2.0 gf/denier or more.

5. The article of claim 3, wherein said fiber has a titer of 700 denier or more.

6. The article of claim 3, wherein said fiber has a wicking height of at least 35 mm after 30 minutes.

7. The article of claim 3, wherein said fiber is a dental floss.

8. The article of claim 3, wherein said fiber has a porosity of less than 30%.

* * * * *